US006290731B1

United States Patent
Solovay et al.

(10) Patent No.: US 6,290,731 B1
(45) Date of Patent: *Sep. 18, 2001

(54) AORTIC GRAFT HAVING A PRECURSOR GASKET FOR REPAIRING AN ABDOMINAL AORTIC ANEURYSM

(75) Inventors: Kenneth S. Solovay, Fort Lauderdale; Robert P. Letendre, Miami, both of FL (US)

(73) Assignee: Cordis Corporation, Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/050,347

(22) Filed: Mar. 30, 1998

(51) Int. Cl.[7] ................................................. A61F 2/06
(52) U.S. Cl. ......................................... 623/51.16; 623/1.35
(58) Field of Search ................................ 623/1, 1.1, 1.11, 623/1.12, 1.13, 1.15, 1.16, 1.19, 1.21, 1.35, 1.36

(56) References Cited

U.S. PATENT DOCUMENTS

| | | | |
|---|---|---|---|
| 4,317,451 | 3/1982 | Cerwin et al. | 128/325 |
| 4,553,545 | 11/1985 | Maass | 128/341 |
| 4,580,568 | 4/1986 | Gianturco | 128/345 |
| 4,655,771 | 4/1987 | Wallsten | 625/1 |
| 4,665,906 | 5/1987 | Jervis | 128/92 |
| 4,681,110 | 7/1987 | Wiktor | 128/343 |
| 4,732,152 | 3/1988 | Wallsten | 128/343 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 4,784,137 | 11/1988 | Kulik et al. | 128/334 |
| 4,875,480 | 10/1989 | Imbert | 128/343 |
| 4,907,336 | 3/1990 | Gianturco | 29/515 |
| 4,950,227 | 8/1990 | Savin | 604/8 |
| 4,990,151 | 2/1991 | Wallsten | 606/108 |
| 5,026,377 | 6/1991 | Burton | 606/108 |
| 5,045,072 | 9/1991 | Castillo | 604/280 |
| 5,159,920 | 11/1992 | Cordon | 128/6 |
| 5,219,355 | 6/1993 | Parodi | 606/191 |
| 5,304,197 | 4/1994 | Pinchuk | 606/194 |
| 5,316,023 | 5/1994 | Palmaz | 128/898 |
| 5,318,535 | 6/1994 | Miraki | 604/102 |
| 5,360,443 | 11/1994 | Barone | 623/1 |
| 5,411,507 | 5/1995 | Heckele | 606/108 |

(List continued on next page.)

FOREIGN PATENT DOCUMENTS

| | | | |
|---|---|---|---|
| 0 657 147 A2 | 10/1994 | (EP) | A61F/2/06 |
| 783 873 | 7/1997 | (EP) | A61F/2/06 |
| 880 948 | 12/1998 | (EP) | A61F/2/06 |

(List continued on next page.)

*Primary Examiner*—David H. Willse
*Assistant Examiner*—Aluin Stewart

(57) ABSTRACT

In accordance with the present invention there is provided a pre-cursor stent for positioning within the infrarenal neck, between an abdominal aortic aneurysm and the renal arteries, of a patient to assist in repairing the abdominal aortic aneurysm. The stent designed to be coupled to a graft for directing blood flow. The graft has a distal end for positioning distal to the aneurysm, and a proximal end for positioning proximal to the aneurysm. The precursor stent includes a substantially cylindrical expandable member having a proximal end, a distal end and an interior. The stent further includes a compressible gasket member located within the interior of the expandable member and attached thereto. The compressible member is substantially impervious to water when in a compressed state. In addition, the stent has a means, within the compressible member, for coupling the graft to the gasket member. This is so the coupled device can direct blood flow therethrough, with the gasket member substantially preventing blood from flowing into the aneurysm.

43 Claims, 10 Drawing Sheets

U.S. PATENT DOCUMENTS

| | | | |
|---|---|---|---|
| 5,476,506 | 12/1995 | Lunn | 623/1 |
| 5,480,423 | 1/1996 | Ravenscroft | 623/1 |
| 5,484,444 | 1/1996 | Braunschweiler | 606/108 |
| 5,507,769 | 4/1996 | Marin et al. | 606/198 |
| 5,522,880 * | 6/1996 | Barone et al. | 623/1 |
| 5,562,724 | 10/1996 | Vorwerk et al. | 623/1 |
| 5,571,170 * | 11/1996 | Palmaz et al. | 623/1 |
| 5,571,171 | 11/1996 | Barone | 623/1 |
| 5,571,173 | 11/1996 | Parodi | 623/1 |
| 5,578,071 | 11/1996 | Parodi | 623/1 |
| 5,578,072 | 11/1996 | Barone | 623/1 |
| 5,591,229 | 1/1997 | Parodi | 623/1 |
| 5,628,788 | 5/1997 | Pinchuk | 623/1 |
| 5,632,763 | 5/1997 | Glastra | 606/194 |
| 5,639,278 * | 6/1997 | Dereume et al. | 623/1 |
| 5,653,745 | 8/1997 | Trescony et al. | 623/1 |
| 5,676,696 | 10/1997 | Marcade | 623/1 |
| 5,683,449 | 11/1997 | Marcade | 623/1 |
| 5,693,084 | 12/1997 | Chuter | 623/1 |
| 5,693,085 * | 12/1997 | Buirge et al. | 623/1 |
| 5,702,418 | 12/1997 | Ravenscroft | 606/198 |
| 5,749,880 | 5/1998 | Banas | 606/198 |
| 5,755,773 * | 5/1998 | Evans et al. | 623/1 |
| 5,760,006 | 6/1998 | Shank | 514/23 |
| 5,823,198 * | 10/1998 | Jones et al. | 128/899 |
| 5,824,040 | 10/1998 | Cox et al. | 623/1 |
| 5,824,042 | 10/1998 | Lombardi et al. | 623/1 |
| 5,843,160 | 12/1998 | Rhodes | 623/1 |
| 5,855,598 | 1/1999 | Pinchuk | 623/1 |
| 5,980,565 | 11/1999 | Jayaraman | 623/1 |
| 5,993,481 | 11/1999 | Marcade et al. | 623/1 |
| 6,039,749 | 3/2000 | Marin et al. | 606/198 |
| 6,070,589 | 6/2000 | Keith et al. | 128/898 |
| 6,090,128 * | 7/2000 | Douglas | 606/198 |
| 6,110,198 * | 8/2000 | Fogarty et al. | 623/1.12 |

FOREIGN PATENT DOCUMENTS

| | | | |
|---|---|---|---|
| 2 743 293 | 1/1996 | (FR) | A61F/2/06 |
| WO 87/04935 | 8/1987 | (WO) | A61M/29/00 |
| WO95/16406 | 6/1995 | (WO) | A61F/2/06 |
| WO95/21592 | 8/1995 | (WO) | A61F/2/06 |
| 97/33532 | 9/1997 | (WO) | A61F/2/06 |
| WO98/07389 | 2/1998 | (WO) | A61F/2/06 |
| 9807389 * | 2/1998 | (WO) | 623/1 |
| WO 99/11199 | 3/1999 | (WO) | A61F/2/06 |

* cited by examiner

AORTIC GRAFT HAVING A PRECURSOR GASKET FOR REPAIRING AN ABDOMINAL AORTIC ANEURYSM

FIELD OF THE INVENTION

The invention relates to an aortic graft for intraluminal delivery, and a method and apparatus for repairing an abdominal aortic aneurysm.

BACKGROUND OF THE INVENTION

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a membrane, the peritoneum. The aorta is the main trunk, or artery, from which the systemic arterial system proceeds. It originates from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm will eventually cause rupture of the sac with ensuing fatal hemorrhaging in a very short time. High mortality associated with the rupture has led to the present state of the art and the trans-abdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of either DACRON®, TEFLON®, or other suitable material.

To perform the surgical procedure requires exposure of the aorta through an abdominal incision, which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aorta aneurysm, the survival rate of treated patients is markedly higher than if the surgery is performed after the aneurysm ruptures, although the mortality rate is still quite high. If the surgery is performed prior to the aneurysm rupturing, the mortality rate is typically less than 5%. Conventional surgery performed after the rupture of the aneurysm is significantly higher, one study reporting a mortality rate of 66.7%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate, are: the extended recovery period associated with such surgery; difficulties in suturing the graft, or tube, to the aorta; the loss of the existing thrombosis to support and reinforce the graft; the unsuitability of the surgery for many patients having abdominal aortic aneurysms; and the problems associated with performing the surgery on an emergency basis after the aneurysm has ruptured. As to the extent of recovery, a patient can expect to spend from 1 to 2 weeks in the hospital after the surgery, a major portion of which is spent in the intensive care unit, and a convalescence period at home from 2 to 3 months, particularly if the patient has other illness such as heart, lung, liver, and/or kidney disease, in which case the hospital stay is also lengthened. Since the graft must be secured, or sutured, to the remaining portion of the aorta, it is often difficult to perform the suturing step because of thrombosis present on the remaining portion of the aorta, and that remaining portion of the aorta wall may be friable, or easily crumbled.

Since the thrombosis is totally removed in the prior art surgery, the new graft does not have the benefit of the previously existing thrombosis therein, which could be utilized to support and reinforce the graft, were the graft to be able to be inserted within the existing thrombosis. Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such surgery, which is considered major surgery. Such patients have difficulties in surviving the operation. Lastly, once the aneurysm has ruptured, it is difficult to perform conventional surgery on an expedited basis because of the extent of the surgery.

Accordingly, the prior art teaches various methods and apparatus for repairing an abdominal aortic aneurysm which is believed to lower morbidity and mortality rate by not requiring an abdominal incision and general anesthesia, not requiring suturing the graft to the remaining aortic wall, and which permits the existing aortic wall and thrombosis therein to be retained to reinforce and support the aortic graft. An example of such a method and apparatus is given in U.S. Pat. No. 5,316,023 issued to Palmaz et al. on May 31, 1994; U.S. Pat. No. 5,360,443 issued to Barone et al. on Nov. 1, 1994; U.S. Pat. No. 5,578,071 issued to Parodi on Nov. 26, 1996; and U.S. Pat. No. 5,591,229 issued to Parodi on Jan. 7, 1997, all of which are hereby incorporated herein by reference.

Devices, such as the one shown in the above referenced Barone patent, use an improved method for repairing an abdominal aortic aneurysm in an aorta having two iliac arteries associated therewith. The device includes first and second tubes, preferably made from a variety of materials such as DACRON® and other polyester materials, TEFLON® (polytetrafluoroethylene), TEFLON® coated DACRON®, porous polyurethane, silicone, expanded polytetrafluoroethylene, and expanded polyurethane. It is preferred that all of the foregoing materials be porous to allow for an intimal layer to form on the tubes 160. Each of the tubes are connected to expandable and deformable, tubular members, or stents. These stents can be similar in structure to those described in disclosed in U.S. Pat. No. 4,733,665 issued on Mar. 29, 1988; U.S. Pat. No. 4,739,762, issued on Apr. 26, 1988; and U.S. Pat. No. 4,776,337 issued on Oct. 11, 1988, all of the foregoing patents being in the name of Julio C. Palmaz, each of which is incorporated herein by reference. Each of the tube/stent structures are then disposed on the end of a balloon catheter. Either both tubes are inserted into the same femoral artery or one of the tubes is inserted into one femoral artery of the patient and the other tube is inserted into the other femoral artery of the patient. Thereafter the tubes are intraluminally delivered to the aorta, thereby disposing at least a portion of each tube within the abdominal aortic aneurysm. The balloon catheters are then expanded to expand and deform the tubular members, to force the tubular members radially outwardly into contact with the aorta and each other. This secures the tubular members and a least a portion of each tube within the aorta, whereby the tubes provide a bilateral fluid passageway through the abdominal aortic aneurysm.

While the above mentioned devices would seem to work well, there is a desire to improve them. More particularly, there is a need to ensure that most of the blood flowing through the abdomen, flows through the bilateral fluid passageways and not around them where it could cause further damage. An improved device should to try to limit the amount of blood which could leak around the bilateral fluid passageways and into the aneurysm. The present invention provides for such an improved device.

SUMMARY OF THE INVENTION

In accordance with the present invention there is provided a pre-cursor stent for positioning within the infrarenal neck, between an abdominal aortic aneurysm and the renal arteries, of a patient to assist in repairing the abdominal aortic aneurysm. The stent is designed to be coupled to a graft for directing blood flow. The graft has a distal end for positioning distal to the aneurysm, and a proximal end for positioning proximal to the aneurysm. The precursor stent includes a substantially cylindrical expandable member having a proximal end, a distal end and an interior. The stent further includes a compressible gasket member located within the interior of the expandable member and attached thereto. The compressible member is substantially impervious to blood when in a compressed state. In addition, the stent has a means, within the compressible member, for coupling the graft to the gasket member. This is so the coupled device can direct blood flow through the graft, with the gasket member substantially preventing blood from flowing into the aneurysm.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE INVENTION

Figure 1:
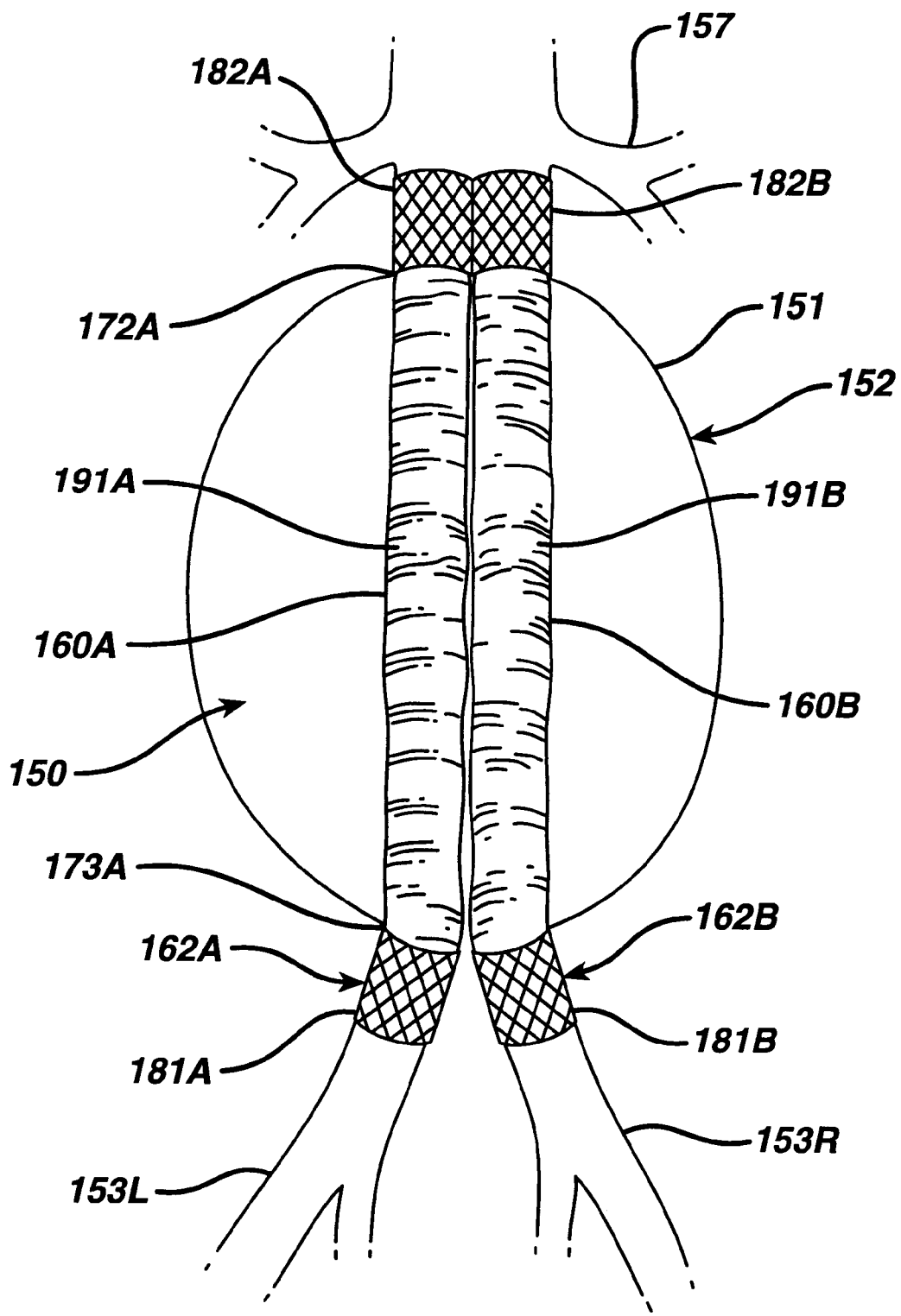
FIG. 1 is a partial cross-sectional view a prior art bilateral intra-aortic bypass graft of the type to be used with the present invention.

The present invention is designed to be coupled and/or used with a graft for directing blood flow. Referring now to the drawings, wherein like numerals indicate the same element throughout the views, there is shown in FIG. 1, a prior art version of such a graft. The type of graft it is designed to be coupled to is very similar to types of grafts known in the prior art. Therefore, a description of a prior art graft may be helpful. FIG. 1 shows such a graft. FIG. 1 shows a bilateral intra-aortic bypass graft 150 for intraluminal delivery to repair an abdominal aortic aneurysm 151 in an aorta 152 having two iliac arteries 153L, 153R associated therewith. Associated with aorta 152, above aneurysm 151, are a plurality of renal arteries 157, in fluid communication with aorta 152. Bilateral intra-aortic bypass graft 150, as well as other grafts to be hereinafter described, could also be utilized in the thoracic aorta, and can be used to repair thoracic aneurysms or thoracic dissecting aneurysms. Accordingly, use of the term "aortic aneurysm" in this specification and claims is intended to relate to and mean both abdominal aortic aneurysms and thoracic aneurysms.

Bypass graft 150 is seen to generally comprise a first graft tube 160A having distal and proximal ends 172A and 173A, at least a portion of the graft tube 160A adapted to be disposed within the aneurysm 151, preferably so that its distal end is distal to the aneurysm and its proximal end is proximal to the aneurysm. A second graft tube 160B is similarly situated on the right side. Graft 150 also includes first and second tubular stent members 162A, 162B, each having proximal and distal ends 181A & 181B, and 182A & 182B located within grafts 160. Each stent member 162A, 162B has proximal and distal ends, preferably positioned so that the distal ends are distal to the aneurysm and the proximal ends are proximal to the aneurysm.

The stent members 162, along with graft tubes 160 permit intraluminal delivery into the aorta 152. This is accomplished by percutaneously inserting the stent members into the same or different femoral arteries and navigating them into the aorta. This type of procedure is similar to delivery of angioplasty catheters and guiding catheters into the human vasculature. Once the stent members are properly positioned they are deployed either through a radially, outwardly extending force, such as a balloon catheter, or self-expanding stents and deployed by releasing the stent members from a constraint. Once deployed, a bilateral passageway is formed within the abdominal aortic aneurysm by passageways 191A, 191B extending through the stent members 162 and graft tubes 160 forming a generally inverted Y-shaped configuration. Each stent member 162A, 162B preferably has a smooth outer wall surface disposed between its distal and proximal ends. Stent members 162 preferably have a substantially uniform thickness with a plurality of slots formed therein.

Graft tubes 160A, 160B preferably have a generally, circular cross-sectional configuration, and can be made from a variety of materials, provided they have the requisite strength characteristics to be utilized as a bypass graft 150, as well as have the requisite compatibility with the human body in order to be used as a graft, or implant material, without being rejected by the patient's body. Examples for such materials are DACRON Registered™ and other polyester materials, TEFLON Registered™ (polytetrafluoroethylene), TEFLON Registered™ coated DACRON Registered™, porous polyurethane, silicone, expanded polytetrafluoroethylene, and expanded polyurethane. It is preferred that all of the foregoing materials be porous to allow for an intimal layer to form on the graft tubes 160. Additionally, graft tubes 160A, 160B can be made by the replamineform replicated life forms process, which is a method for fabricating uniformly microporous materials from marine skeletal structures. The foregoing described fabric materials can be knitted or woven, and can be warp or weft knitted. If the material is warp knitted, it may be provided with a velour, or towel like surface, which speeds up clotting of blood which contacts graft tubes 160A, 160B in order to increase the attachment, or integration, of graft tubes 160A, 160B to aorta 152, or to assist the integration of graft tubes 160A, 160B to the thrombosis 154. Graft tubes 160A, 160B can also be made of a biodegradable, or degradable material, such as albumin or collagen or a collagen coated material. A graft tube which is bioerodible, would erode and dissolve, or degrade, over a period of time; however, it is believed that a layer of endothelium, or skin, will grow as the graft tubes 160A, 160B erode, the new layers of endothelium, or skin, provide a new, fluid impervious lining within aneurysm 151. In some procedures, it might be desirable to make graft tubes 160A, 160B of a fluid impervious material. Additionally, graft tubes 160A, 160B or stent 162A, 162B, could have a coating of a biologically inert material, such as TEFLON Registered™ or porous polyurethane.

If any of the foregoing described materials are used for the manufacture of graft tubes 160, the graft tubes may be connected to the stent members 162 by a plurality of conventional sutures of polypropylene, DACRON Registered™, or any other suitable material. Preferably, the ends of graft tubes 160 overlap and cover the second ends of stent members 162, such overlapping being approximately 50% of the length of stent members 162.

Figure 2:
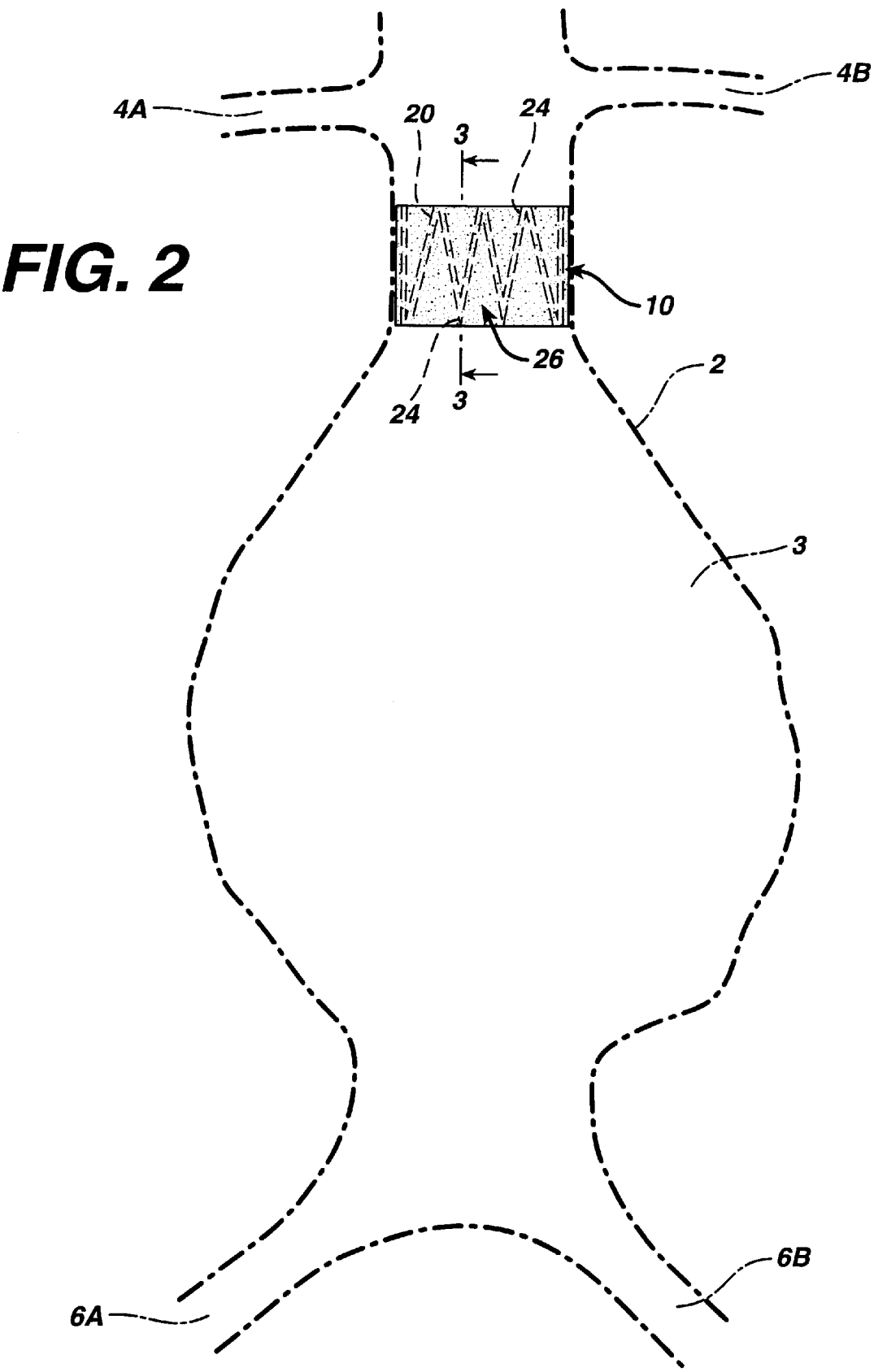
FIG. 2 is a partial cross section of the aorta, abdominal aortic aneurysm, and iliac vessels illustrating the placement of the precursor stent of the present invention in place in the aorta.

The present invention improves upon the prior art graft 150, mentioned above, by further including, and preferably initially deploying, a precursor stent 10, shown in FIG. 2. FIG. 2 shows an aorta 2, an abdominal aortic aneurysm 3, renal arteries 4A and 4B, iliac vessels 6A and 6B and a precursor stent 10 made in accordance with the present invention. Stent 10 is shown in its fully deployed condition and in its preferred position, between the abdominal aortic aneurysm 3, and the renal arteries 6A and 6B. Stent 10 includes a substantially cylindrical expandable member 20 having a proximal end 22, a distal end 24 and an interior 26. Member 20 has a collapsed state for insertion into the target area, and an expanded condition for deployment into the target area.

Figure 12:
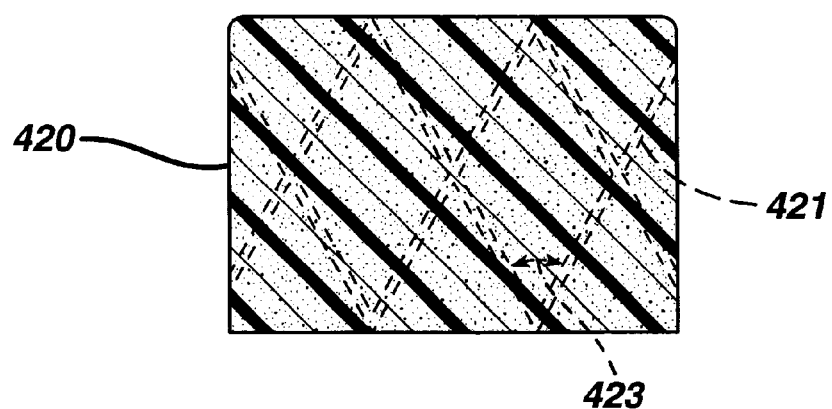
FIG. 12 is a side view of an alternative embodiment of a pre-cursor stent made in accordance with the present invention.

Member 20 is shown in the figures as being a simple zigzag stent. Member 20 can take on many different patterns or configurations and can be made similarly to a balloon expandable or self expanding stent which are widely known to those of ordinary skill in the art. One preferred embodiment, shown in FIG. 12, comprises an expandable member 420 having a plurality, preferably 8, of diamond shapes 421 connected to each other. When the stent is fully expanded, the diamonds would have angles 423 of 45–55 degrees at their distal and proximal ends. Referring back to FIG. 2, if member 20 is balloon expandable, it is typically made by a laser cutting holes or a pattern in a stainless steel tube. Examples of such devices are found in U.S. Pat. No. 4,733,665 issued to Palmaz on Mar. 29, 1988, and U.S. Pat. No. 4,776,337 issued to Palmaz on Oct. 11, 1988, both of which are hereby incorporated herein by reference. Member 20 can also be a self-expanding member or stent. Self expanding stents are typically made from superelastic Nickel Titanium alloys (Nitinol). Descriptions of medical devices which use such alloys can be found in U.S. Pat. No. 4,665,906 issued to Jervis on May 19, 1987, which is hereby incorporated herein by reference.

Figure 3:
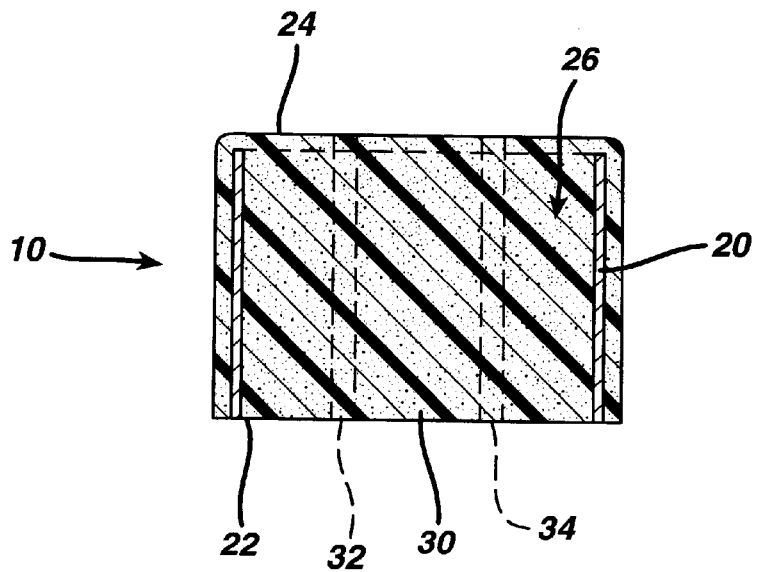
FIG. 3 is a cross section of the precursor stent taken along line 3—3 of FIG. 2.

Stent 10 can be better understood by referring to FIG. 3 which shows a cross-section of the stent taken along lines 3—3 in FIG. 2. As seen from that figure, precursor stent 10 further includes a gasket member 30. Gasket member 30 should be located within the expandable member 20 such that it would come in the way of or impede any blood trying to flow through the interior of the expandable member 20. For this exemplory embodiment gasket member 30 comprises a compressible member located within the interior 26 of the expandable member 20. For the exemplary embodiment shown in FIG. 3, gasket member 30 can be made from any number of materials known to those of ordinary skill in the art including open cell foam materials such as polyurethane, polyethylene, polytetrafluroethylene, other various polymeric materials which are woven or knitted to provide a flexible structure such as Dacron, polyurethane, polypropylene, polytetrafluroethylene can also be used. Gasket member 30 can be attached to expandable member 20 by any number of means including a plurality of conventional sutures of polypropylene, DACRON®, or any other suitable material and attached thereto. Other methods of attaching gasket 30 to expandable member include adhesives, ultrasonic welding, mechanical interference fit. Alternatively, gasket member 30 could be inserted within the expandable member 20 after the expandable member has been deployed.

As will be explained later herein, it is preferable that the compressible member is substantially impervious to the flow of blood, at least when in a partially compressed state. When used throughout for the present invention, materials which are substantially impervious to the flow of blood include materials which become substantially impervious to the flow of blood after being saturated with blood. When the stent tubes and graft members, described above, are inserted and expanded within the gasket member 30, the gasket member 30 will compress. In this state, the gasket should be substantially impervious to blood so as to prevent blood from flowing through the interior 26 of expandable member 20 and into the aneurysm.

The stent should include, within the compressible member, a coupling for joining a bilateral graft, such as graft 150, to the gasket member. As seen from FIG. 3, stent 10 includes two substantially cylindrical conduits (although they could have any suitable shape), 32 and 34, extending through gasket 30. Conduits 32 and 34 are designed to receive one half of a bilateral graft in its un-expanded condition. After the grafts are inserted into the conduits, they are expanded so that they are attached to stent 10. However, conduits 32 and 34 are not the only coupling for joining a bilateral graft, such as graft 150, to the gasket member. The coupling could be an integral part of the material the gasket 30 is made from. For example if gasket 30 is made from an open cell foam, the bilateral graft could pierce the material so as to effectively create its own conduit through the gasket 30. The coupling does not have to be a physical attachment, but rather some means for allowing the stents and grafts to work in operational engagement. This coupling is so that the combined precursor stent and bilateral graft direct blood flow through the graft, with the gasket member substantially preventing blood from flowing into the aneurysm.

Figure 4:
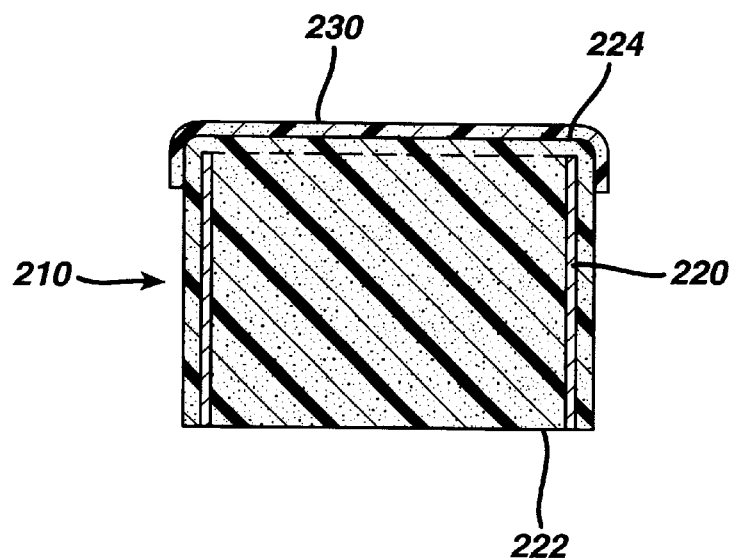
FIG. 4 is a view similar to that of FIG. 3 but showing an alternative embodiment of the precursor stent made in accordance with the present invention.

An alternative embodiment of the present invention is shown in FIG. 4. FIG. 4 shows precursor stent 210, which is similar to stent 10. Precursor stent 210 includes an expandable member 220, similar to expandable member 20. Stent 210 includes a compressible gasket member 230 attached to the distal end 224 of member 220. Gasket 230 may extend along the full length of the member 220 from its distal end to its proximal end. Gasket 230 when deployed, as well as gasket 30, is a means, between the distal ends of each graft member 172 A and 172B, and between the distal ends of the graft members (172A & 172B) and the arterial wall, for substantially preventing blood from flowing through any gaps between the distal ends 172 A & 172B of grafts 160, and between those distal ends and the arterial wall. Other means include the other embodiments shown in the drawings, foams, gels, other materials which are injected or otherwise placed around the distal ends of the grafts, either before or after the grafts have been fully deployed.

Gasket 230 is similar to a drum gasket. Gasket member 230 can be made from any number of materials known to those of ordinary skill in the art including various polymeric materials which are woven, knitted, or foamed to provide a flexible structure such as polyurethane, polyethylene, polytetrafluroethylene, other various polymer materials which are woven or knitted to provide a flexible structure such as Dacron, polyurethane, polypropylene, polytetrafluroethylene can also be used. Gasket 230 can be attached to expandable member 220 by any number of means including a plurality of conventional sutures of polypropylene, DACRON®, or any other suitable material and attached thereto. Other methods of attaching gasket 20 to expandable member 20 include adhesives, ultrasonic welding, mechanical interference fit. Stent 210 should also include a coupling for joining the bilateral graft to the gasket member. Gasket 330 could include two substantially circular holes, similar to conduits 32 and 34, extending through gasket 230. The coupling could also be an integral part of the material the gasket 230 is made from. For example if gasket 30 is made from an open cell foam the bilateral graft could be pierce the material so as to effectively create its own conduit through the gasket 230. This coupling is so that the combined precursor stent and bilateral graft direct blood flow through the graft, with the gasket member substantially preventing blood from flowing into the aneurysm.

Figure 5:
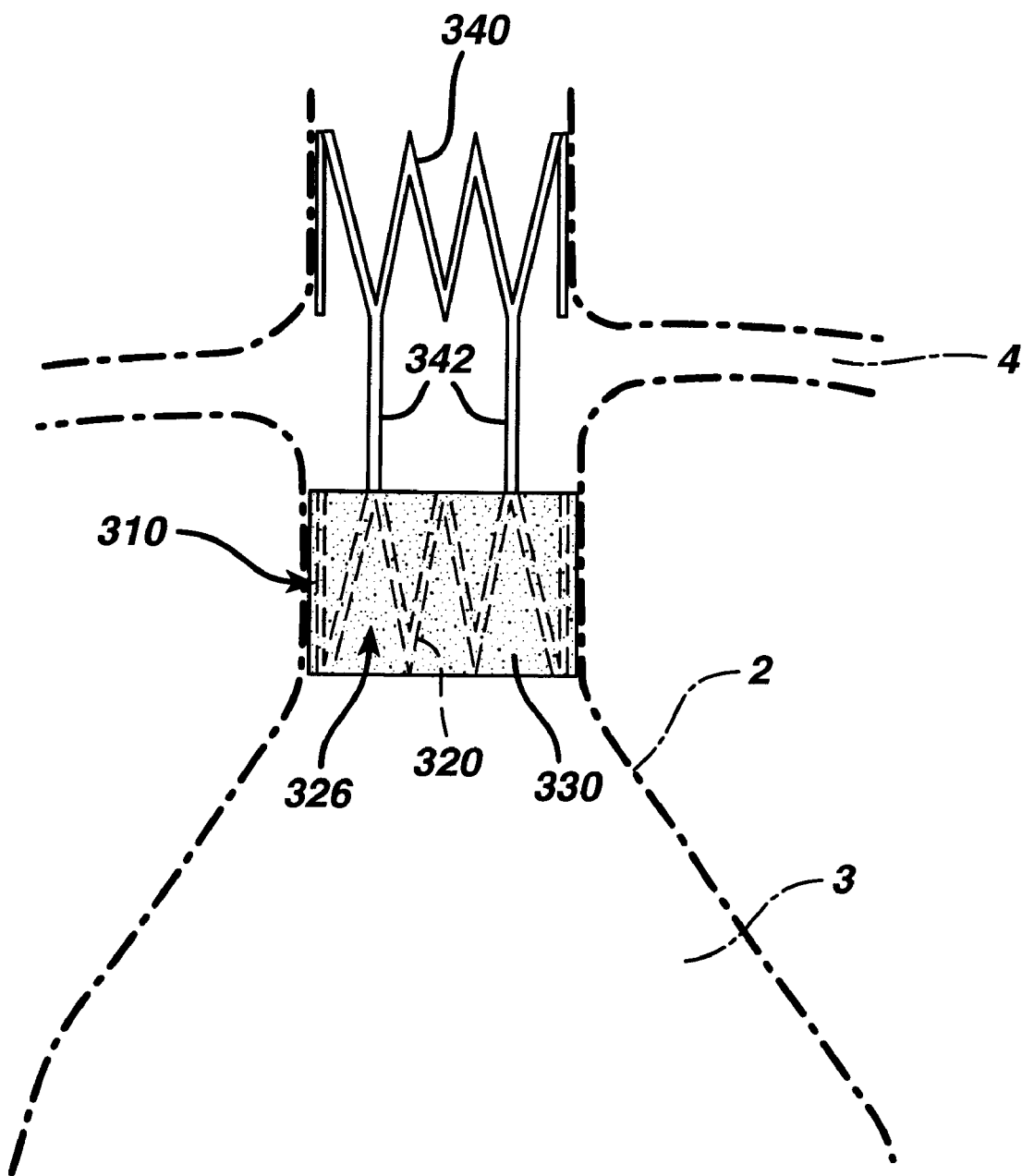
FIG. 5 is a view similar to that of FIG. 1 but showing an alternative embodiment of the precursor stent made in accordance with the present invention.

Yet another alternative embodiment of the present invention is shown in FIG. 5. FIG. 5 shows a precursor stent 310, similar to stent 10, made in accordance with the present invention. Stent 310 includes an expandable member 320 and a compressible gasket member 330 located within the interior 326 of the expandable member 320. Expandable member 320 is similar to expandable member 20, except that it includes an anchoring stent 340. Anchoring stent 340 is basically an additional expandable member, located distal to expandable member 320 and connected thereto by struts 342. Stent 340 has an open interior and is preferably placed aorta distal to the renal arteries 4. The anchoring stent is particularly useful where the length of the aorta 2 distal to the aneurysm 3 is less than half the length of the expandable member 320. Often in these instances additional anchoring is required to secure the precursor stent 310 in position.

Figure 6:
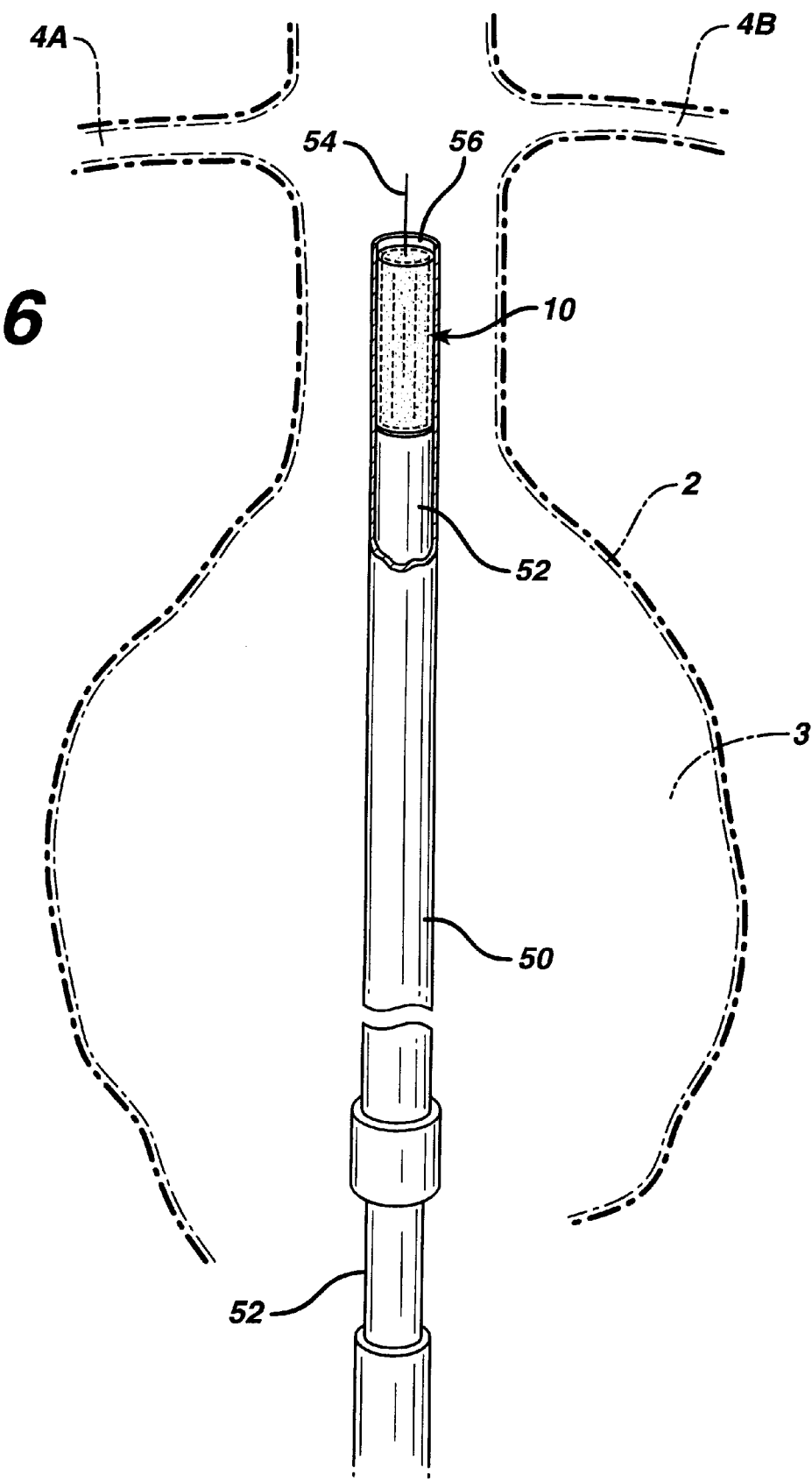
FIG. 6 is a partial cross section of the aorta, abdominal aortic aneurysm, and iliac vessels with precursor stent-gasket positioned in its delivery catheter for deployment.
Figure 7:
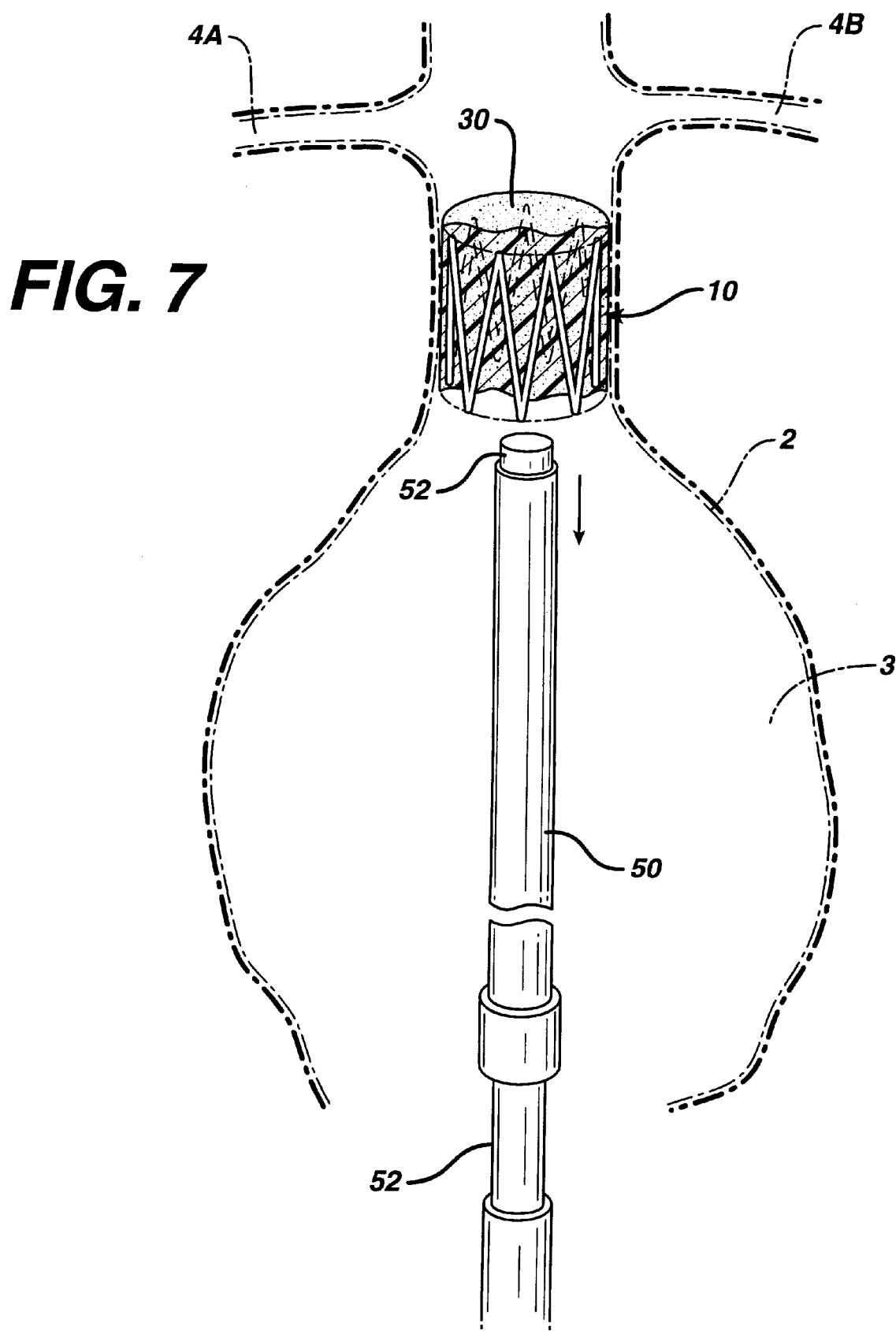
FIG. 7 is a view similar to that of FIG. 6 but showing the precursor stent 10 in its deployed position.

A description of how the present invention is deployed into the body can best be understood by first referring to FIG. 6. For this description we will assume that expandable member 20 is a self-expanding member made from superelastic Nitinol. As seen from this figure, the precursor stent-gasket assembly 10 is compressed into a delivery catheter 50, and the delivery catheter is delivered percutaneously through the femoral artery and into the abdomen. Delivery catheter can be similar to commercially available guiding catheters, such as the one described in U.S. Pat. No. 5,045,072 issued to Castillo et al. on Sep. 3, 1991, which is hereby incorporated herein by reference. A pusher 52 is also in position inside the delivery catheter 50 proximal to the precursor stent-gasket assembly 10 such that it can be used to advance the precursor stent-gasket assembly 10 out of the open end 56 of delivery catheter 50 by either advancing the catheter proximally while the pusher 52 remains stationary, by advancing the pusher distally while the catheter remains stationary, or by simultaneous proximal and distal movement of the catheter and pusher. As will be appreciated by those skilled in the art, the pusher 52 may have an elongated extension which goes through the stent 10 to provide an access lumen for a guidewire. In one preferred embodiment the pusher 52 may comprise a lumen for passage of a guidewire 54 to facilitate the initial positioning of the delivery catheter 50. FIG. 7 shows the stent 10 after it has been deployed.

Figure 8:
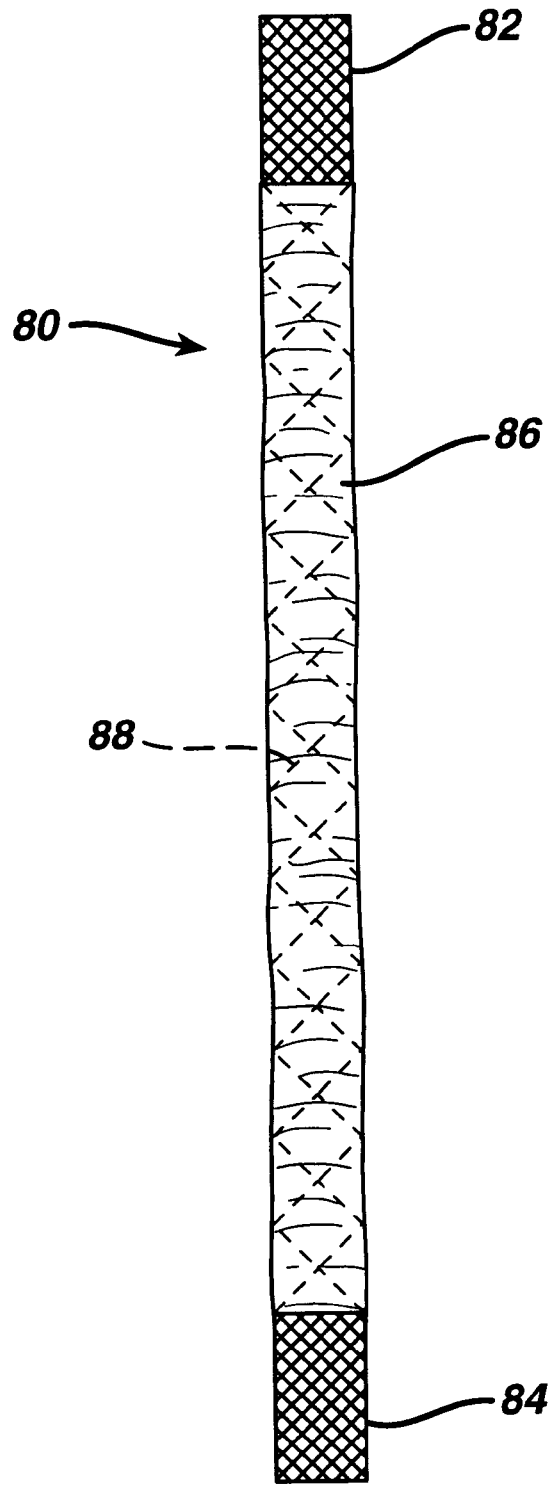
FIG. 8 is a plan view of a preferred endograft in accordance with the present invention.

After the precursor stent 10 has been deployed, a bilateral graft, similar to that shown in FIG. 1, is then deployed. FIG. 8 shows a preferred embodiment of a graft tube and stent member to be used in accordance with the present invention. FIG. 8 shows an endograft 80 which has a similar function but a different construction than the graft tube 160 and stent member 162 combination described above. Two of these endografts would make up a bilateral graft assembly. Endograft 80 comprises a distal anchoring stent 82, a proximal anchoring stent 84, and a flexible graft tube 86 extending therebetween. The two anchoring stents 82 and 84 are expandable from a compressed state to the proper size, much in the same way precursor stent 10 is deployed. Distal anchoring stent 82 is designed to sealably contact and attach itself to the gasket member 30, while proximal anchoring stent 84 is designed to be expanded so as to make contact with and attach itself to an iliac artery. Anchoring stents 82 and 84 can be self-expanding stents or plastically deformable balloon expandable stents, both types being discussed above. Graft tube 86 can be made from any of the materials graft member 160 can be made from. Preferred materials include a polymer material woven, spun, knitted, or other fabrication process obvious to those familiar with the art. Graft tube 86 is preferably impermeable to the flow of blood or becomes impermeable to blood flow therethrough after it is saturated. Graft tube 86 must be flexible to contour to the anatomy and of sufficient strength to sustain physiological blood pressure.

One preferable feature of the graft tube 86 is a scaffold 88. Scaffold 88 can be similar in structure to stent members 162 described above. Scaffold 88 may be incorporated within the graft tube 86 or attached to the inside or outside of the graft tube 86. In an additional embodiment the scaffold 88 and anchoring stents 82 and 84 are made from a single structure. This single structure could be made from a balloon expandable material or a self-expanding material such as Nitinol.

When the single structure is made from Nitinol, its delivery would be substantially similar to the delivery of stent 10 when it is made from a self-expanding material, such delivery is described herein.

Figure 9:
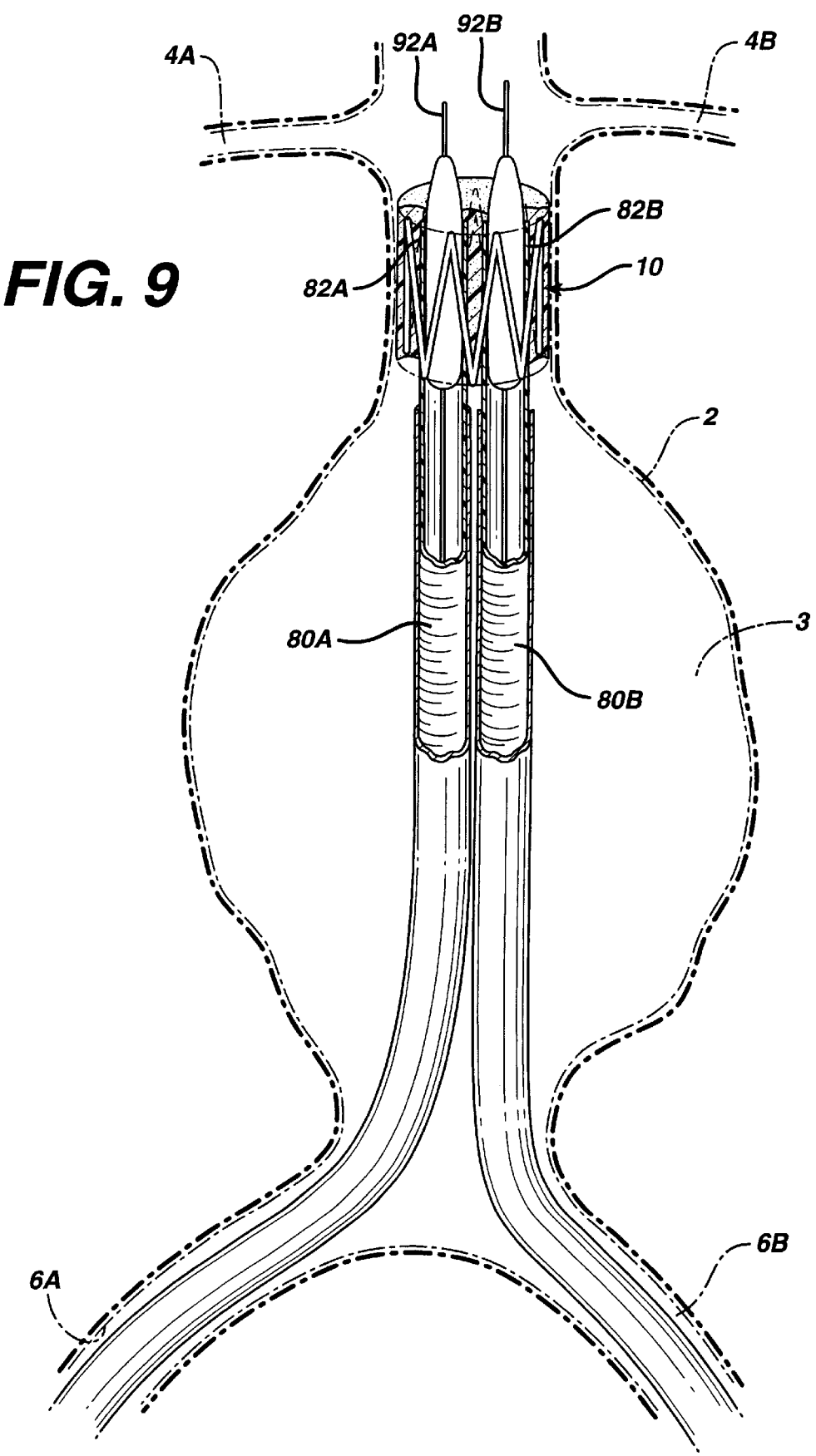
FIG. 9 is a view similar to that of FIG. 7, but showing the endografts on their delivery catheters in position for deployment.

How these endografts are implanted after precursor stent 10 is deployed can best be understood by referring to FIG. 9. As seen from this figure, the bilateral endografts 80A and 80B are navigated to the abdomen. This would be accomplished by mounting the distal anchoring stents 82A and 82B onto balloon catheters 90A and 90B and thereafter percutaneously inserting the catheters into a femoral artery and navigating the endografts to the target site. Guidewires 92A and 92B can be used to help delivery of the balloon catheter to the target site. Navigating balloon catheters within the human arterial system, with or without stents mounted thereon, is well known in the art. An example of a balloon catheter is given in U.S. Pat. No. 5,304,197 issued to Pinchuck et al. on Apr. 19, 1994, which is hereby incorporated herein by reference. In this preferred embodiment, the anchoring stents 82 are plastically deformable and made from a material such as stainless steel. The proximal anchoring stents 84 may be introduced separately after placement of the distal anchoring stents 82 or may be integral to the scaffold 12.

Figure 10:
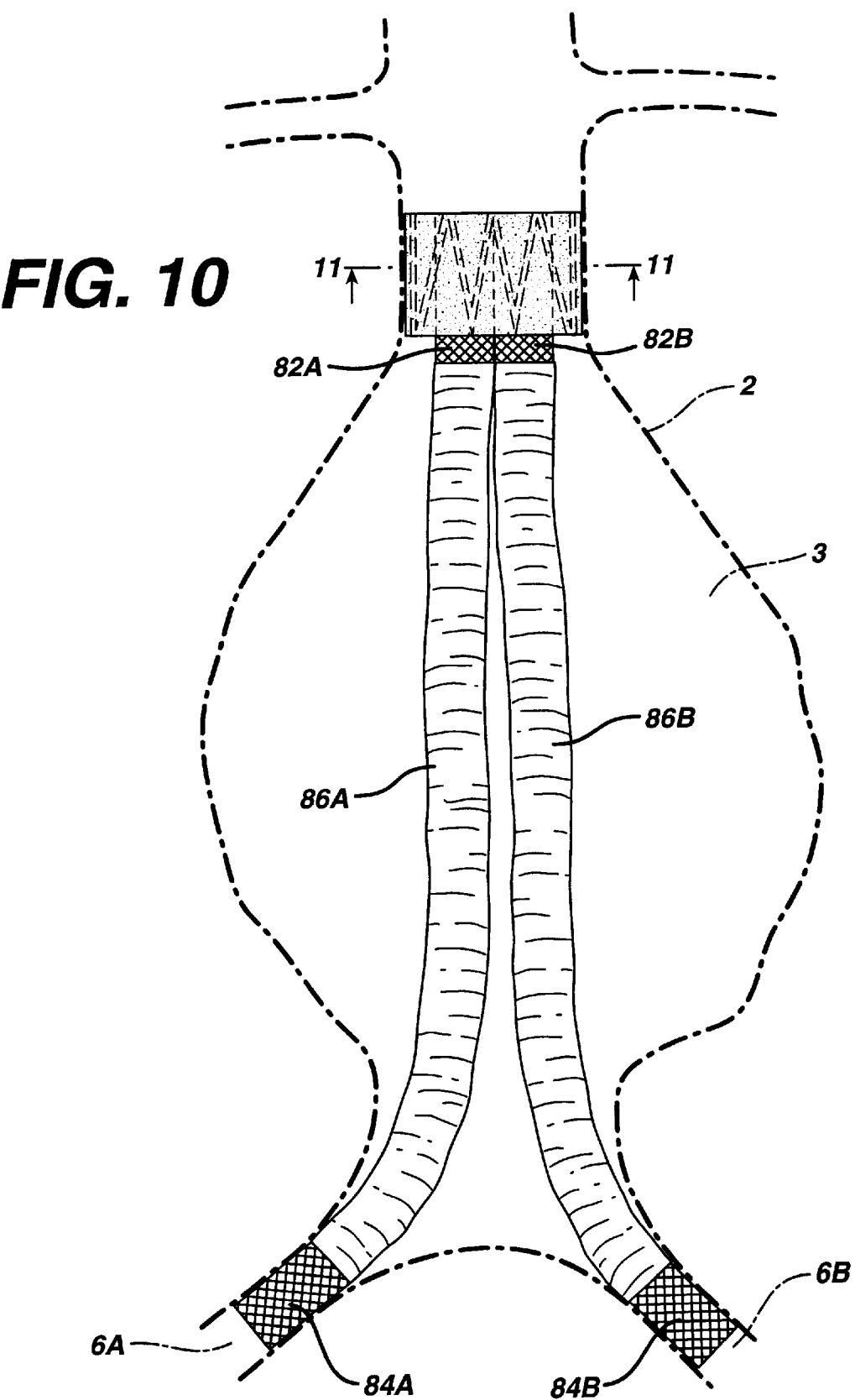
FIG. 10 is a view similar to that of FIG. 9 but showing the endografts in their deployed position.
Figure 11:
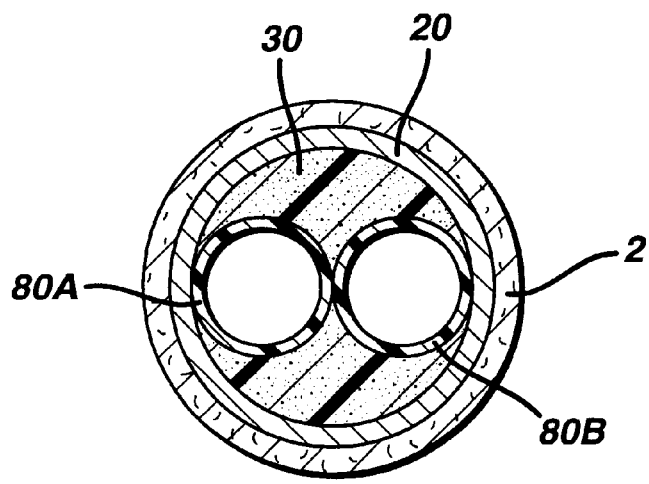
FIG. 11 is a cross-sectional view taken along line 11—11 of FIG. 10.

FIG. 10 shows how the entire system looks after the precursor stent 10, and anchoring stents 82 and 84 have been deployed. FIG. 11 is a good illustration of how the present invention substantially prevents blood from flowing around endografts 86 and into the abdomen. As seen from that figure, expandable member 20 makes contact with the aorta 3 when it is expanded, and gasket member 30 fills the space between the bilateral endografts 80A and 80B and the aorta 3 this creating a seal which directs substantially all of the blood flow through the endografts.

Although particular embodiments of the present invention have been shown and described, modification may be made to the device and/or method without departing from the spirit and scope of the present invention. The terms used in describing the invention are used in their descriptive sense and not as terms of limitations.

What is claimed is:

1. An aortic graft for intravascular delivery to repair an abdominal aortic aneurysm in an aorta having two iliac arteries associated therewith, said graft comprising:
   a) first and second stents having distal and proximal ends, each stent is designed to be inserted through a femoral artery in a collapsed condition, and inserted within the aneurysm where said stent is expanded, said distal ends of said stents being distal to said aneurysm adjacent an arterial wall, said first and second stents are covered at least partially by tubular graft members, each said tubular graft member extending into an iliac artery when said stents are deployed; and
   b) a means, between said distal ends of each of said stents and between said distal ends of said stents and said arterial wall, for substantially preventing blood from flowing through any gaps between said distal ends of said first and second stents, and between said distal ends of said first and second stents and said arterial wall.

2. The aortic graft of claim 1 wherein said first and second stents are self-expanding stents.

3. The aortic graft of claim 2 wherein said first and second stents are made from a superelastic Nickel-Titanium alloy.

4. The aortic graft of claim 1 wherein said means, between said distal ends of each of said stents and between said distal ends of said stents and said arterial wall, for substantially preventing blood from flowing through any gaps between said distal ends of said first and second stents, and between said distal ends of said first and second stents and said arterial wall comprises a third stent for positioning within an infrarenal neck, between an abdominal aortic aneurysm and the renal arteries, said third stent comprising:
   a) a substantially cylindrical expandable member having a proximal end, a distal end and an interior;
   b) a gasket member which is substantially impervious to blood flow, said gasket member is attached to said expandable member such that it will impede blood flow through said interior of said expandable member.

5. The aortic graft of claim 4, wherein said gasket member comprises a compressible member located with said interior of said expandable member.

6. The aortic graft of claim 5 wherein said gasket member comprises an open cell foam.

7. The aortic graft of claim 5 wherein said gasket member includes two conduits extending therethrough, said conduits are in operational engagement with said first and second stents for directing blood flow through said first and second stents.

8. The aortic graft of claim 4 wherein said gasket member comprises a member attached to said expandable member, said member covering said distal end of said expandable member.

9. The aortic graft of claim 4 wherein said expandable member is a self-expanding stent.

10. The aortic graft of claim 8 wherein said expandable member is made from a superelastic nickel-titanium alloy.

11. The aortic graft of claim 4 wherein said expandable member is a balloon expandable stent.

12. An aortic graft for intravascular delivery to repair an abdominal aortic aneurysm in an aorta having two iliac arteries associated therewith, said graft comprising:
   a) first and second graft members having distal and proximal ends, each graft member is designed to be inserted through a femoral artery in a collapsed condition, and inserted within the aneurysm and deployed therein, said distal ends of said graft members being distal to said aneurysm adjacent an arterial wall; and
   b) a gasket, between said distal ends of each of said graft members and between said distal ends of graft members and said arterial wall, for substantially preventing blood from flowing through any gaps between said distal ends of said graft members, and between said distal ends of said graft members and said arterial wall.

13. The aortic graft of claim 12 wherein each of said graft members further includes an expandable stent attached to said distal end of said graft member for securing said graft within a body of a patient.

14. The aortic graft according to claim 13 wherein said expandable stent extends substantially along the entire length of said graft.

15. The aortic graft according to claim 13 wherein each of said graft members further includes an expandable stent attached to said proximal end of said graft for securing said graft member within a body of a patient.

16. The aortic graft of claim 13 wherein said stents are self-expanding stents.

17. The aortic graft of claim 16 wherein said stents are made from a superelastic Nickel-Titanium alloy.

18. The aortic graft of claim 12 wherein said gasket, between said distal ends of each of said graft members and between said distal ends of said stents and said arterial wall, for substantially preventing blood from flowing through any gaps between said distal ends of said graft members, and between said distal ends of said graft members and said arterial wall comprises a third stent for positioning within an infrarenal neck, between an abdominal aortic aneurysm and the renal arteries, said third stent comprising:

a) a substantially cylindrical expandable member having a proximal end, a distal end and an interior;

b) a gasket member which is substantially impervious to blood flow, said gasket member is attached to said expandable member such that it will impede blood flow through said interior of said expandable member.

19. The aortic graft of claim 18, wherein said gasket member comprises a compressible member located with said interior of said expandable member and attached to said expandable member.

20. The aortic graft of claim 19 wherein said gasket member includes two conduits extending therethrough, said conduits are in operational engagement with said graft members for directing blood flow through said graft members.

21. The aortic graft of claim 19 wherein said gasket member comprises an open cell foam.

22. The aortic graft of claim 18 wherein said gasket member comprises a member attached to said expandable member, said member covering said distal end of said expandable member.

23. The aortic graft of claim 18 wherein said expandable member is a self-expanding stent.

24. The aortic graft of claim 23 wherein said expandable member is made from a superelastic nickel-titanium alloy.

25. The aortic graft of claim 18 wherein said expandable member is a balloon expandable stent.

26. A pre-cursor stent for positioning within the infrarenal neck, between an abdominal aortic aneurysm and the renal arteries, of a patient to assist in repairing the abdominal aortic aneurysm, said stent designed to be coupled to grafts for directing blood flow through a bifurcation in the artery, said grafts having distal ends for positioning distal to said aneurysm, and proximal ends for positioning proximal to said aneurysm, said pre-cursor stent comprising;

a) a substantially cylindrical expandable member having a proximal end, a distal end and an interior;

b) a gasket member which is substantially impervious to blood flow, said gasket member is attached to said expandable member such that it will impede blood flow through said interior of said expandable member.

27. The precursor stent of claim 26 further including a means, within said gasket member, for coupling said graft to said gasket member so as to direct blood flow therethrough, whereby said gasket member substantially prevents blood from flowing into an aneurysm.

28. The aortic graft of claim 27 wherein said means, within said gasket member, for coupling said graft to said gasket member so as to direct blood flow therethrough comprises at least one conduits extending through said gasket member.

29. The aortic graft of claim 26, wherein said gasket member comprises a compressible member located with said interior of said expandable member.

30. The aortic graft of claim 29 wherein said gasket member comprises an open cell foam.

31. The aortic graft of claim 26 wherein said gasket member comprises a member attached to said expandable member, said member covering said distal end of said expandable member.

32. The aortic graft of claim 26 wherein said expandable member is a self-expanding stent.

33. The aortic graft of claim 32 wherein said expandable member is made from a superelastic nickel-titanium alloy.

34. The aortic graft of claim 26 wherein said expandable member is a balloon expandable stent.

35. The aortic graft of claim 26 further including an anchoring stent distal to said expandable member, said anchoring stent is attached to said expandable member by at least one strut.

36. A pre-cursor stent for positioning within the infrarenal neck, between an abdominal aortic aneurysm and the renal arteries, of a patient to assist in repairing the abdominal aortic aneurysm, said stent designed to be coupled to grafts for directing blood flow through a bifurcation in the artery, said grafts having distal ends for positioning distal to said aneurysm, and proximal ends for positioning proximal to said aneurysm, said pre-cursor stent comprising;

a) a substantially cylindrical expandable member made from a superelastic nickel-titanium alloy having a proximal end, a distal end and an interior;

b) a gasket member which is substantially impervious to blood flow, said gasket member is attached to said expandable member such that it will impede blood flow through said interior of said expandable member; and c) a means, within said gasket member, for coupling said grafts to said gasket member so as to direct blood flow therethrough, whereby said gasket member substantially prevents blood from flowing into an aneurysm.

37. The aortic graft of claim 36 wherein said means, within said gasket member, for coupling said graft to said gasket member so as to direct blood flow therethrough comprises at least one conduits extending through said gasket member.

38. The aortic graft of claim 36, wherein said gasket member comprises a compressible member located with said interior of said expandable member and attached to said expandable member.

39. The aortic graft of claim 38 wherein said gasket member comprises an open cell foam.

40. The aortic graft of claim 36 wherein said gasket member comprises a member attached to said expandable member, said member covering said distal end of said expandable member.

41. The aortic graft of claim 36 wherein said expandable member is a self-expanding stent.

42. The aortic graft of claim 36 wherein said expandable member is a balloon expandable stent.

43. The aortic graft of claim 36 further including an anchoring stent distal to said expandable member, said anchoring stent is attached to said expandable member by at least one strut.

\* \* \* \* \*